US006485523B2

(12) United States Patent
Pierce et al.

(10) Patent No.: US 6,485,523 B2
(45) Date of Patent: Nov. 26, 2002

(54) GOLF PROSTHESIS

(75) Inventors: William A. Pierce, Dallas, TX (US); John W. Stephenson, Dallas, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 0 days.

(21) Appl. No.: 09/785,355

(22) Filed: Feb. 16, 2001

(65) Prior Publication Data

US 2002/0116074 A1 Aug. 22, 2002

Related U.S. Application Data

(60) Provisional application No. 60/228,834, filed on Aug. 28, 2000.

(51) Int. Cl.$^7$ ................................................. A61F 2/68
(52) U.S. Cl. ........................................................ 623/65
(58) Field of Search ............................ 623/65; 473/131

(56) References Cited

U.S. PATENT DOCUMENTS

| | | | | |
|---|---|---|---|---|
| 3,747,128 A | | 7/1973 | De Filipo | 3/12.8 |
| 4,357,717 A | * | 11/1982 | Puhl | 3/128 |
| 4,661,113 A | * | 4/1987 | Adkins | 623/65 |
| 5,464,444 A | * | 11/1995 | Farquharson et al. | 623/65 |

OTHER PUBLICATIONS

Internet—TRS Inc.—Prosthetics Research, Design & Manufacturing, located at website: www.oandp.com/commerci/trs/, printed Sep. 9, 1999.
Internet—TRS Family of Specialized Sports/Recreational Adaptors, located at website: www.oandp.com/commerci/trs/sports.htm , printed Sep. 9, 1999.
Brochure by Gripping Aid Hand Wrap of elastic hand wrap; date not known precisely but believed to be in Applicants' possession prior to Jan. 1, 2000.
Article, *Arch Phys Med Rehabil*, vol. 63, Jul. 1982 by Ram P. Bhala, MD, and Charles F. Schultz, CP entitled "Golf Club Holder for Upper–extremity Amputee Golfers", together with photos of prosthetic device cited by Ram P. Bhala, MD taken by Applicant.

* cited by examiner

*Primary Examiner*—Bruce Snow
(74) *Attorney, Agent, or Firm*—Vinson & Elkins, L.L.P.

(57) ABSTRACT

A golf prosthesis assisting an upper extremity amputee to swing a golf club. In one embodiment, the prosthesis comprises first and second prosthetic sockets in which the amputee's limbs are received. An extension pylon extends from the first prosthetic socket towards the golf club. The second prosthetic socket is attached to the extension pylon, thereby assisting the amputee in keeping shoulders, back and hips in proper alignment during back swing and return swing. There is also a more complete transfer of energy into the swing from the shoulders, back and legs. A wrist terminal device connects the extension pylon to the golf club. The wrist terminal device emulates cocking and release of the wrists during a conventional golf swing. The wrist terminal device provides a club holder firmly holding the golf club, and a rotary joint advantageously restrained from rotation in all but a preselected plane. The preselected plane is adjustably selectable with respect to the direction in which the amputee desires to hit the ball. The rotary joint permits predetermined amounts of rotation during back swing and return swing. In one set of embodiments, rotation in the preselected plane is encouraged by spring action to return to a rest position in which the golf club extends substantially straight towards the ball and away from the amputee when the amputee addresses the ball before swinging.

59 Claims, 6 Drawing Sheets

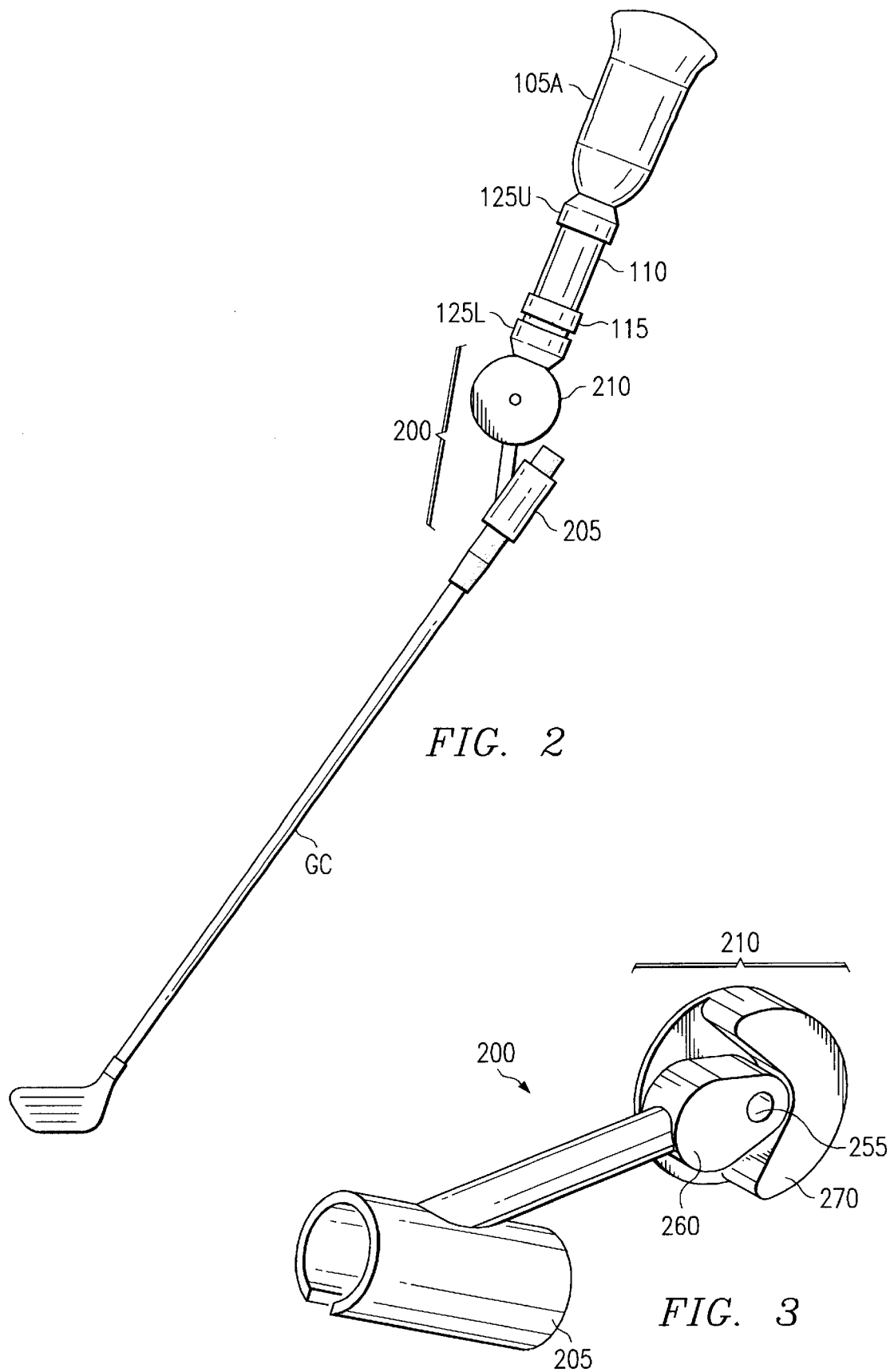

GOLF PROSTHESIS

RELATED APPLICATION

This application claims priority under 35 U.S.C. §119(e) to U.S. provisional patent application No. 60/228,834, filed Aug. 28, 2000.

TECHNICAL FIELD OF THE INVENTION

This invention relates generally to prosthetic devices enabling an upper extremity amputees to play golf, and more specifically to a golf prosthesis that includes a slidable mechanism and a wrist emulator mechanism that allow the amputee to swing a golf club in a manner that resembles a conventional golf swing.

BACKGROUND OF THE INVENTION

It is well known in the health care field that therapeutic benefits can be gained by enabling persons with physical handicaps to play conventional sports. Such is the case with enabling upper extremity amputees to play golf The therapeutic benefits are both physical and psychological.

Golf is a difficult game for an upperextremity amputee to master, especially when the amputee has only partial use of both upper extremities. It is well known in the golf art that the coordinated movement of shoulders, back and legs during a golf swing is communicated to the club via the arms and hands, and particularly the wrists.

Prior art golf prostheses are known assisting an amputee who has partially lost the use of one upper extremity only. There is therefore a need for a prosthesis assisting the amputee who has partially lost the use of both upper extremities.

The prior art golf prostheses also assume that the amputee has a "good" hand for use as the primary grip on the club in a conventional swing (i.e. the left hand for a right handed player and the right hand for a left handed player). These prior art prostheses are not serviceable for an amputee who has lost the partial use of both upper extremities, or who otherwise does not have a "good" hand for use as a primary grip on the club. There is therefore a need in the art for a prosthesis which emulates the action of the hand and wrist which is the primary grip on the club in a conventional swing.

The fact that these prior art prostheses assume that the amputee has a "good" hand also causes them to overlook another problem facing amputees who have lost partial use of both upper extremities. The gripping of two hands together on a golf club in a conventional swing assists the golfer in keeping shoulders, back and hips in proper alignment during back swing and return swing. Clearly this body alignment is unavailable to an upper extremity amputee unless both limbs are connected to the golf club. Further, the use of both of hands in a conventional swing allows a more complete transfer of energy from the back, shoulders and legs into the golf swing. There is therefore a need in the art for a prosthesis including a mechanism that emulates keeping both hands on the club during back swing and return swing.

SUMMARY OF THE INVENTION

These and other objects and advantages are achieved by a golf prosthesis assisting an upper extremity amputee to swing a golf club. In one embodiment, the prosthesis comprises first and second prosthetic sockets in which the amputee's limbs are received. An extension pylon extends from the first prosthetic socket towards the golf club. The second prosthetic socket is slidably engaged upon the extension pylon, thereby assisting the amputee in keeping shoulders, back and hips in proper alignment during back swing and return swing. A wrist terminal device connects the extension pylon to the golf club. The wrist terminal device emulates cocking and release of the wrists during a conventional golf swing. The wrist terminal device provides a club holder firmly holding the golf club, and a rotary joint restrained from rotation in all but a preselected plane. The preselected plane is adjustably selectable with respect to the direction in which the amputee desires to hit the ball. In some embodiments, rotation in the preselected plane is encouraged by spring action to return to a rest position in which the golf club extends substantially straight towards the ball and away from the amputee when the amputee addresses the ball before swinging. The rotary joint permits selectable amounts of rotation against the spring action during back swing and return swing.

One embodiment of the invention thus provides a golf prosthesis for an upper extremity amputee, the prosthesis assisting the amputee to swing a golf club, the prosthesis comprising first and second prosthetic sockets, an extension pylon extending from the first prosthetic socket towards the golf club, the second prosthetic socket attached to the extension pylon, and a wrist terminal device connecting the extension pylon to the golf club; the wrist terminal device further including a club holder, the club holder firmly holding the golf club, a rotary joint restrained from rotation in all but a preselected plane, the preselected plane adjustably selectable with respect to the direction in which the amputee desires to hit a ball with the golf club, and the rotary joint permitting predetermined amounts of rotation during back swing and return swing. In further embodiments, rotation in the preselected plane is encouraged by spring action to return to a rest position in which the golf club extends substantially straight towards the ball and away from the amputee when the amputee addresses the ball before swinging.

Another embodiment of the invention provides a golf prosthesis for an upper extremity amputee, the prosthesis assisting the amputee to swing a golf club, the prosthesis comprising a prosthetic socket and a wrist terminal device connecting the prosthetic socket to the golf club; the wrist terminal device further including a club holder, the club holder firmly holding the golf club, a rotary joint, rotation of the rotary joint encouraged by spring action to return to a rest position in which the golf club extends substantially straight towards a ball and away from the amputee when the amputee addresses the ball before swinging, and the rotary joint permitting selectable amounts of rotation against the spring action during back swing and return swing.

Another embodiment of the invention provides a golf prosthesis for an upper extremity amputee, the prosthesis assisting the amputee to swing a golf club, the prosthesis comprising first and second prosthetic sockets, and an extension pylon extending from the first prosthetic socket towards the golf club, the second prosthetic socket attached to the extension pylon. In one further embodiment such attachment is a slidable engagement, and in another further embodiment such attachment is substantially fixed.

Another embodiment of the invention provides a golf prosthesis for an upper extremity amputee, the prosthesis assisting the amputee to swing a golf club, the prosthesis comprising first and second prosthetic sockets, an extension pylon extending from the first prosthetic socket towards the golf club, the second prosthetic socket slidably engaged upon the extension pylon, said slidable engagement of the second prosthetic socket upon the extension pylon including a pylon sleeve disposed to slide along the extension pylon and a connector connecting the pylon sleeve to the second prosthetic socket, and the connector comprising a vibration isolator including a resilient vibration damper made from a material selected from the group consisting of (1) elastomer and (2) rubber.

Another embodiment of the invention provides a golf prosthesis for an upper extremity amputee, the prosthesis assisting the amputee to swing a golf club, the prosthesis comprising first and second prosthetic sockets, an extension pylon extending from the first prosthetic socket towards the golf club, the second prosthetic socket slidably engaged upon the extension pylon, said slidable engagement of the second prosthetic socket upon the extension pylon including a pylon sleeve disposed to slide along the extension pylon and a connector connecting the pylon sleeve to the second prosthetic socket, the connector comprising a vibration isolator including a resilient vibration damper made from a material selected from the group consisting of (1) elastomer and (2) rubber, and a wrist terminal device connecting the extension pylon to the golf club; the wrist terminal device further including a club holder, the club holder firmly holding the golf club, a rotary joint restrained from rotation in all but a preselected plane, the preselected plane adjustably selectable with respect to the direction in which the amputee desires to hit a ball with the golf club, rotation in the preselected plane encouraged by spring action to return to a rest position in which the golf club extends substantially straight towards the ball and away from the amputee when the amputee addresses the ball before swinging, the spring action comprising first and second spring mechanisms encouraging rotation to return to the rest position during back swing and return swing respectively, each of the first and second spring mechanisms including a spring selected from the group consisting of (a) a leaf spring, (b) a ball plunger spring, (c) a pneumatic spring, (d) a hydraulic spring, and (e) a resilient solid material spring, the rotary joint permitting selectable amounts of rotation against the spring action during back swing and return swing, the rotary joint including a rotating portion and a stationary portion, the first and second spring mechanisms each operating upon the rotating portion via leverage against the stationary portion, and the rotary joint further including an adjustable rotation damper mechanism disposed to regulate rotation in response to torque, the rotation damper mechanism comprising a damper ball plunger spring located in the stationary portion of the rotary joint and operable against the rotating portion of the rotary joint, the damper ball plunger spring disposed to be adjustably tightenable in frictionally restraining rotation of the rotating portion.

It is therefore a technical advantage of the present invention to provide a golf prosthesis that assists an amputee who has partially lost the use of both upper extremities, or who otherwise does not have a "good" hand for use as a primary grip on the club.

Another technical advantage of the present invention is to provide a golf prosthesis that includes a mechanism that emulates cocking and release of the wrists during a conventional golf swing.

Another technical advantage of the invention is to provide a golf prosthesis that includes a mechanism emulating keeping both hands on the club during a conventional golf swing. An amputee who has lost partial use of both upper extremities is thus assisted in keeping shoulders, back and hips in proper alignment during back swing and return swing. There is also a more complete transfer of energy into the swing from the shoulders, back and legs.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 2 is a side view as shown on FIG. 1;

FIG. 3 is a perspective view of the rotary joint attached to the club holder;

DETAILED DESCRIPTION OF THE INVENTION

Figure 1:
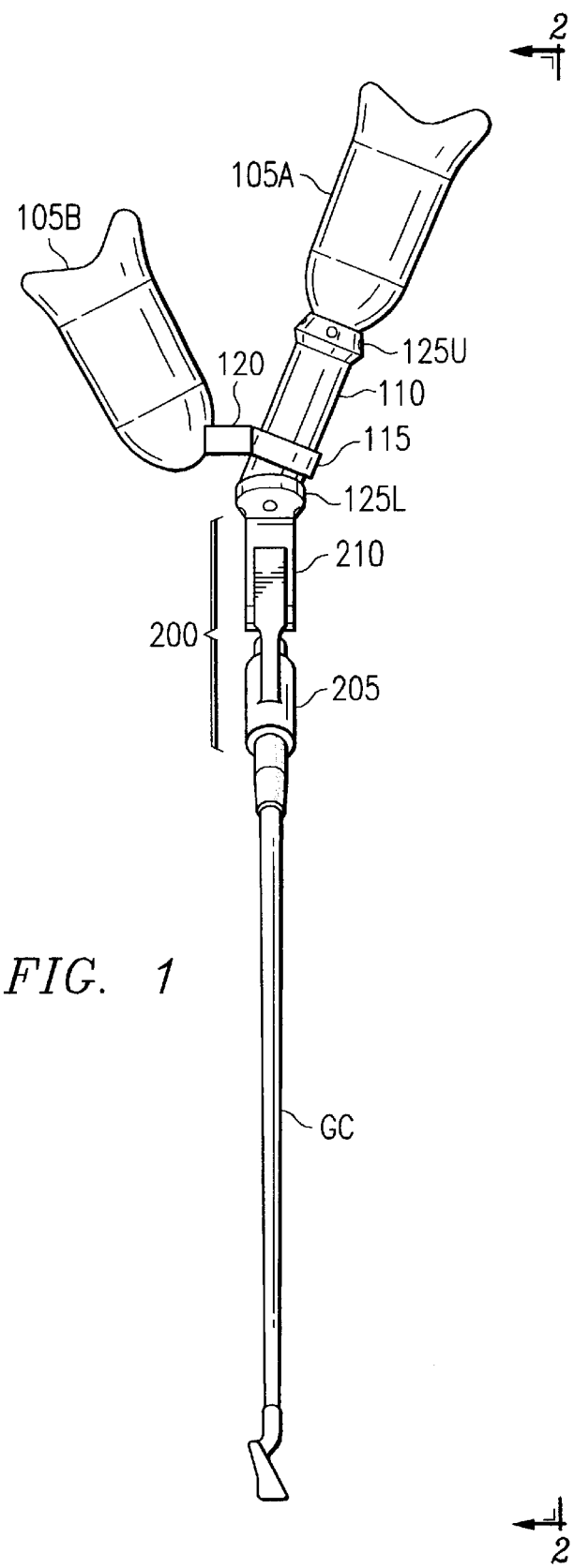
FIG. 1 illustrates the inventive prothesis in a rest position in which an amputee would be addressing a ball on the ground.

FIG. 1 illustrates an embodiment of the inventive golf prosthesis for an upper extremity amputee. In looking at FIG. 1, it should be imagined that the amputee is addressing the ball on the ground prior to commencing a back swing. FIG. 1 is a front view of the inventive prosthesis as worn by the amputee.

It will be seen from FIG. 1 that the prosthesis assists the amputee to swing a golf club. In the rest position illustrated on FIG. 1, the golf club extends substantially straight towards the ball, and away from the amputee. The rest position is further illustrated on FIG. 2, a side view as shown on FIG. 1.

Returning to FIG. 1, first and second prosthetic sockets 105A and 105 B are attached to the amputee's limbs. It will be appreciated that although not illustrated, padding and other suitable material may be placed over the amputee's limbs prior to attaching the prosthetic sockets 105A and 105B so as to optimize comfort and grip by the amputee.

Extension pylon 110 extends from the first prosthetic socket 105A towards the golf club GC. In the embodiment illustrated on FIGS. 1 and 2, the second prosthetic socket 105B is slidably engaged upon the extension pylon 110. Advantageously, as illustrated in FIG. 1, the slidable engagement of the second prosthetic socket 105B upon the extension pylon 110 includes a ring-shaped pylon sleeve 115 disposed to slide along the extension pylon 110, and a connector 120 connecting the pylon sleeve 115 to the second prosthetic socket 105B. It will be appreciated, however, that other well known mechanisms, such as tongue and groove (not illustrated), will obtain substantially the same sliding engagement as illustrated in FIG. 1 to achieve substantially the same result. Further, another embodiment of the inventive prosthesis (not illustrated) simply omits the slidable engagement. Instead, a fixed engagement connects connector 120 to extension pylon 110. In such a fixed embodiment, a vibration isolator such as described immediately below with reference to FIG. 7 becomes highly advantageous to allow small amounts of relative movement between connector 120 and extension pylon 110.

Figure 7:
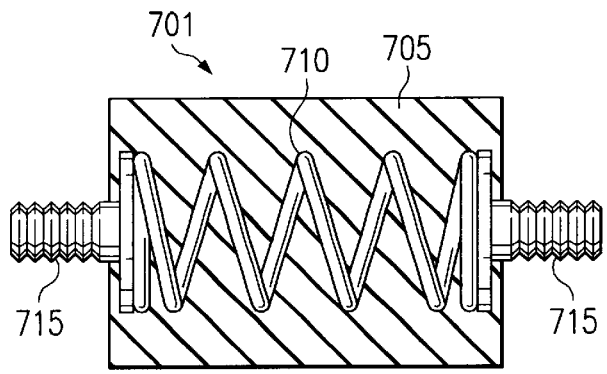
FIG. 7 is a cutaway view of the vibration isolator.

Looking at FIG. 1 and then with reference to FIG. 7, connector 120 advantageously comprises a vibration isolator 701 including a resilient vibration damper 705 made from a suitable material such as an elastomer (e.g. polyurethane) or rubber. FIG. 7 shows a preferred vibration isolator 701 in section, in which a coil spring 710 is also used to dampen vibration. It will be appreciated that other types of well known resilient materials may be used to give vibration damper 705 substantially the same functionality. T-studs 715 at either end of the vibration isolator 701 enable the vibration isolator 701 to be installed in line as part of connector 120 (installation not illustrated).

Although not specifically illustrated, it will also be appreciated that connector 120 may advantageously include a disconnect mechanism operable by the amputee. This disconnect mechanism allows the amputee to disengage the second prosthetic socket from the first prosthetic socket without removing either prosthetic socket. A preferred disconnect mechanism includes a shuttle lock, lever release or twist release operable by the amputee, although it will be appreciated that other types of well known disconnect mechanisms would have an equivalent enabling effect.

It will also be understood that vibration isolator 701 and disconnect mechanism (not illustrated) as described above are optional features providing additional comfort and convenience to an amputee using the inventive prosthesis. It will be appreciated that the inventive prosthesis is nonetheless serviceable without either optional features.

Referring now to FIG. 1 again, wrist terminal device 200 connects the extension pylon 110 to a golf club GC. As can also be seen on FIG. 1, upper and lower tube adaptors 125U and 125L advantageously facilitate connection of the extension pylon 110 to the first prosthetic socket 105A and the wrist terminal device 200 respectively. Although not illustrated, it will be understood that upper and lower tube adaptors 125U and 125L preferably screw onto ends of the extension pylon 110, and further provide screws in a collar disposed to clamp down on faces of a multi-faced lugs provided on the first prosthetic socket 105A and the wrist terminal device 200. It will be appreciated that other well known attachments will also effectively connect the extension pylon 110 to the first prosthetic socket 105A and to the wrist terminal device 200, and that the inventive golf prosthesis is not limited in any way by the preferred attachment described above.

Further, although again not specifically illustrated, it will be appreciated that connector 120 extending from the second prosthetic socket 105B may also include a second extension pylon to extend the amputee's limb from the second prosthetic socket 105B where necessary. Such a second extension pylon may be physically constructed in substantially the same way as extension pylon 110 attached to first prosthetic socket 105A as described above.

Referring now to FIG. 2, it will be seen that many of the features shown on FIG. 1 are also illustrated on FIG. 2, which is a side view as shown on FIG. 1. FIG. 2 further illustrates that wrist terminal device 200 includes club holder 205 disposed to firmly hold the golf club GC. Club holder 205 preferably holds the club firmly by friction (illustrated) or clamping (not illustrated), although it will be understood that the inventive prosthesis is not limited to any particular method of firmly holding the golf club GC.

As shown on FIG. 2, wrist terminal device 200 also includes a rotary joint assembly 210. The rotary joint inside rotary joint assembly 210 is advantageously restrained from rotation in all but a preselected plane adjustably selectable with respect to the direction in which the amputee desires to hit a ball with the golf club GC. Normally this preselected plane will be chosen substantially orthogonal to the direction in which the amputee desires to hit the ball. A degree of selectivity nonetheless allows the amputee to open or close the face of the club for certain shots. It will be seen from FIG. 1 that such selectivity is provided by adjustment of the lower tube adaptor 125L.

Turning now to FIG. 3, it will be appreciated that certain details and features of wrist terminal device 200 are designed to emulate wrist control in a conventional golf swing. As will be explained in greater detail below, the action of the amputee's swing and the momentum of the club head combine to exert torque on the rotary joint (labeled 250 on subsequent illustrations) within rotary joint assembly 210 during the swing. This torque causes rotation of the rotary joint in the preselected plane. As will be seen on FIGS. 4A and 4B, 5 and 6A and 6B, spring action (where provided) nonetheless encourages rotation of the rotary joint 250 in the preselected plane to return to the rest position in which the golf club extends substantially straight towards the ball and away from the amputee when the amputee addresses the ball before swinging.

FIG. 3 illustrates the rotary joint assembly 210 connected to club holder 205. It will be seen on FIG. 3 that rotary joint assembly 210 includes an axle 255, a rotating portion 260 and a stationary portion 270. FIG. 3 illustrates that club holder 205 is advantageously connected integrally with the rotating portion 260. For purposes of embodiments described herein with spring action, it will be understood that such spring action has been omitted from FIG. 3 for clarity.

Figure 4A:
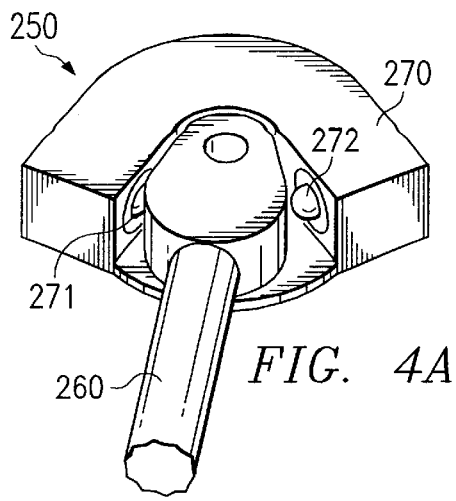
FIG. 4A is a perspective view of the rotaryjoint in a deflected state using ball plunger spring mechanisms.
Figure 4B:
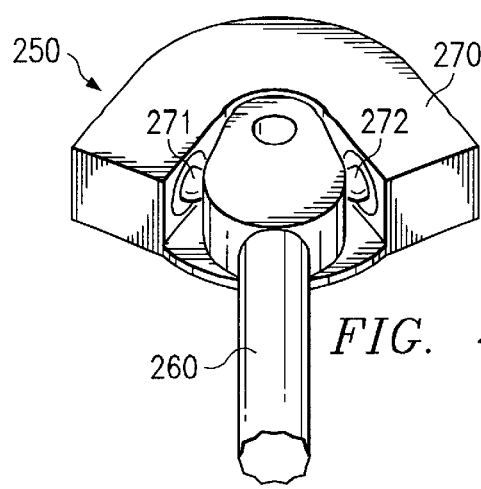
FIG. 4B is a perspective view of the rotary joint in a rest position using ball plunger spring mechanisms.

FIGS. 4A and 4B illustrate operation of spring action on the rotation of rotary joint 250 in an embodiment in which the spring action comprises ball plunger springs. Looking at FIGS. 4A and 4B in more detail, spring action comprises first and second ball plunger spring mechanisms 271 and 272. FIG. 4A illustrates rotary joint 250 in a deflected state, in which rotating portion 260 is engaging first ball plunger spring mechanism 271. It will be seen that first ball plunger spring mechanism 271 is encouraging rotating portion 260 to return to a rest position. In contrast, FIG. 4B illustrates rotary joint 250 in a rest position, held by the opposing encouragements of first and second ball plunger mechanisms 271 and 272. It will thus be seen from FIGS. 4A and 4B that ball plunger spring mechanisms 271 and 272 combine to encourage rotation of the rotary joint 250 return to the rest position.

It will be appreciated that the embodiment of FIGS. 4A and 4B illustrates exemplary use of ball plunger spring mechanisms 271 and 272 as the spring action in rotary joint 250. As will be described in more detail below, however, other spring mechanisms will also enable the spring action with equivalent effect. It will be understood that the invention is not limited to any particular enablement of a spring action in rotary joint 250, so long as deflection in rotating portion 260 is encouraged to a rest position.

Figure 5:
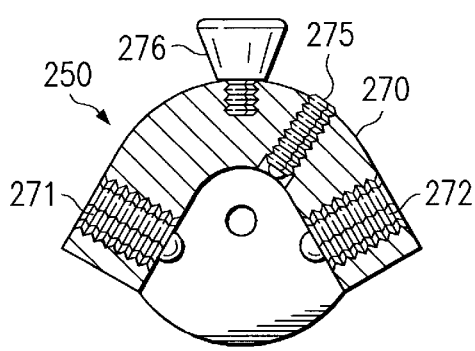
FIG. 5 is a cutaway component view of the stationary portion of the rotary joint in which ball plunger springs are used as spring mechanisms.

FIG. 5 illustrates the components of stationary portion 270 as shown on FIGS. 4A and 4B in detail. It will be understood from FIG. 5 that in an embodiment using exemplary ball plunger spring mechanisms 271 and 272 as shown on FIGS. 4A and 4B, the spring action in rotary joint 250 is advantageously adjustable.

FIG. 5 shows stationary portion 270 cut away to reveal components. Ball plunger spring mechanisms 271 and 272 can be seen in section. Since these types of spring mechanisms are well known in the art, they are not illustrated in great detail. It will be understood that in each mechanism, an adjustment screw engages into stationary portion 270 through the outer wall, and when tightened compresses a coil spring against a ball bearing. The ball bearing bears against a collar or a hole in the inner wall of stationary portion 270, where the diameter of the ball bearing is greater than the diameter of the opening in the collar or hole. Engagement of the ball bearing by the rotating portion 260 thus deflects the ball bearing against the coil spring.

It will therefore be seen from FIGS. 4A, 4B and 5 that the exemplary use of ball plunger spring mechanisms 271 and 272 permits selectable amounts of rotation by rotating portion 260 against the spring action. Tightening or loosening the adjustment screws in ball plunger spring mechanisms 271 and 272 restricts or allows deflection by the ball bearing against the coil spring. The amount of rotation available to rotating portion 260 is thus selectable in response to torque.

FIG. 5 also illustrates a further optional feature to enhance control of the rotation of rotary joint 250 in response to torque developed during back swing and return swing of the golf club. This feature is also operable to adjust the lie of the golf club when addressed to the ball. With further reference to FIG. 5, stationary portion 270 also optionally includes an adjustable rotation damper mechanism 275. Rotation damper mechanism 275 is advantageously another ball plunger spring mechanism of the type described above with respect to items 271 and 272, except that in the case of rotation damper mechanism 275 the ball bearing operates continuously against the rotating portion 260 of the rotary joint 250. When tightened, rotation damper mechanism 275 thus frictionally restrains rotation of the rotating portion 260. Tightening and loosening of the rotation damper mechanism 275 also effects incremental rotation of the rotary joint 250, which can be seen from FIG. 1 to translate into adjustment of the lie of the club GC at the rest position.

FIG. 5 also illustrates a multi-faced lug 276 engaged into stationary portion 270. Referring back to the description above accompanying FIG. 1, it will be appreciated that multi-faced lug is of the type well known in the art that facilitates a suitable connection between wrist terminal device 200 and extension pylon 110 via lower tube adaptor 25L.

Figure 6A:
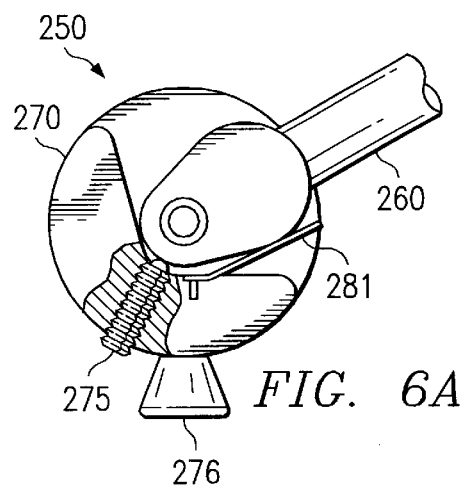
FIG. 6A is a cutaway view of the rotary joint in a deflected state using a leaf spring mechanism.
Figure 6B:
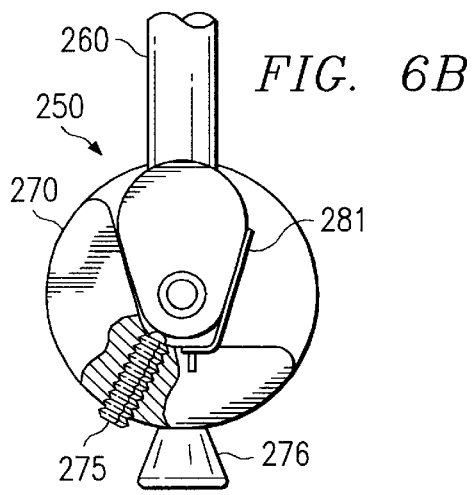
FIG. 6B is a cutaway view of the rotary joint in a rest position using a leaf spring mechanism.

As noted above, it will be appreciated that many other types of well known springs may also be used in enabling spring action in rotary joint 250 against which deflection of rotating portion 260 may operate. FIGS. 6A and 6B illustrate an embodiment in which exemplary use of leaf spring 281 is made. In the embodiment of FIGS. 6A and 6B, only one leaf spring 281 is provided, positioned to become engaged when the amputee reaches the top of the back swing and commences a return swing. FIG. 6A illustrates rotary joint 250 in a deflected state. Leaf spring 281 is encouraging rotating portion 260 to return to a rest position. As previously described above with reference to FIG. 5, optional rotation damper mechanism 275 is shown on FIG. 6A and is operable to frictionally regulate rotation of the rotating portion 260.

FIG. 6B shows the embodiment of FIG. 6A at a rest position. Multi-faced lug 276 is also illustrated on FIGS. 6A and 6B.

It will be appreciated that yet other spring mechanisms are available to encourage rotation of rotary joint 250 to a rest position. The inventive prosthesis is not limited to any particular one, or combination of any particular ones. Such additional spring mechanisms may include, for example, a pneumatic spring, a hydraulic spring, and a resilient solid material spring. Moreover, in another series of embodiments of the invention (such as is discussed above, for example, with respect to FIG. 3), no spring action is provided. Instead, deflection of rotating portion 260 is regulated by rotation damper mechanism 275, if provided, and/or the tempo of the amputee's swing.

Figures 8, 8A:
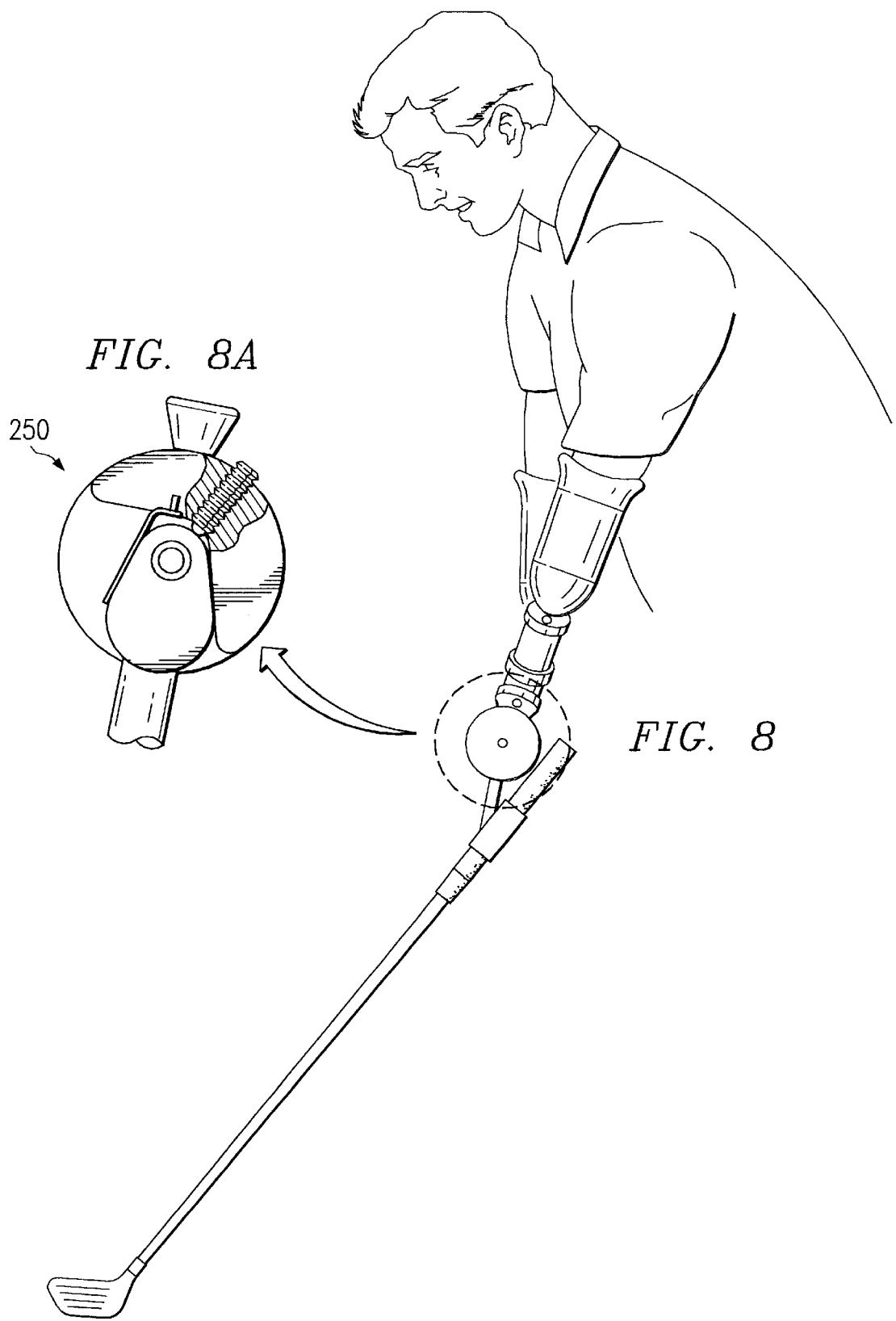
FIGS. 8, 8a, 9, 10 and 10a illustrate operation of the inventive prothesis during a back swing.

FIGS. 8, 8a, 9, 10 and 10a illustrate operation of the inventive prosthesis during use. Starting with FIG. 8, the amputee is addressing the ball at the rest position. FIG. 8a, an inset on FIG. 8, illustrates exemplary use of a leaf spring action in rotary joint 250 as described above with respect to FIGS. 6A and 6B. FIG. 8a shows that rotary joint 250 is at a rest position.

Figure 9:
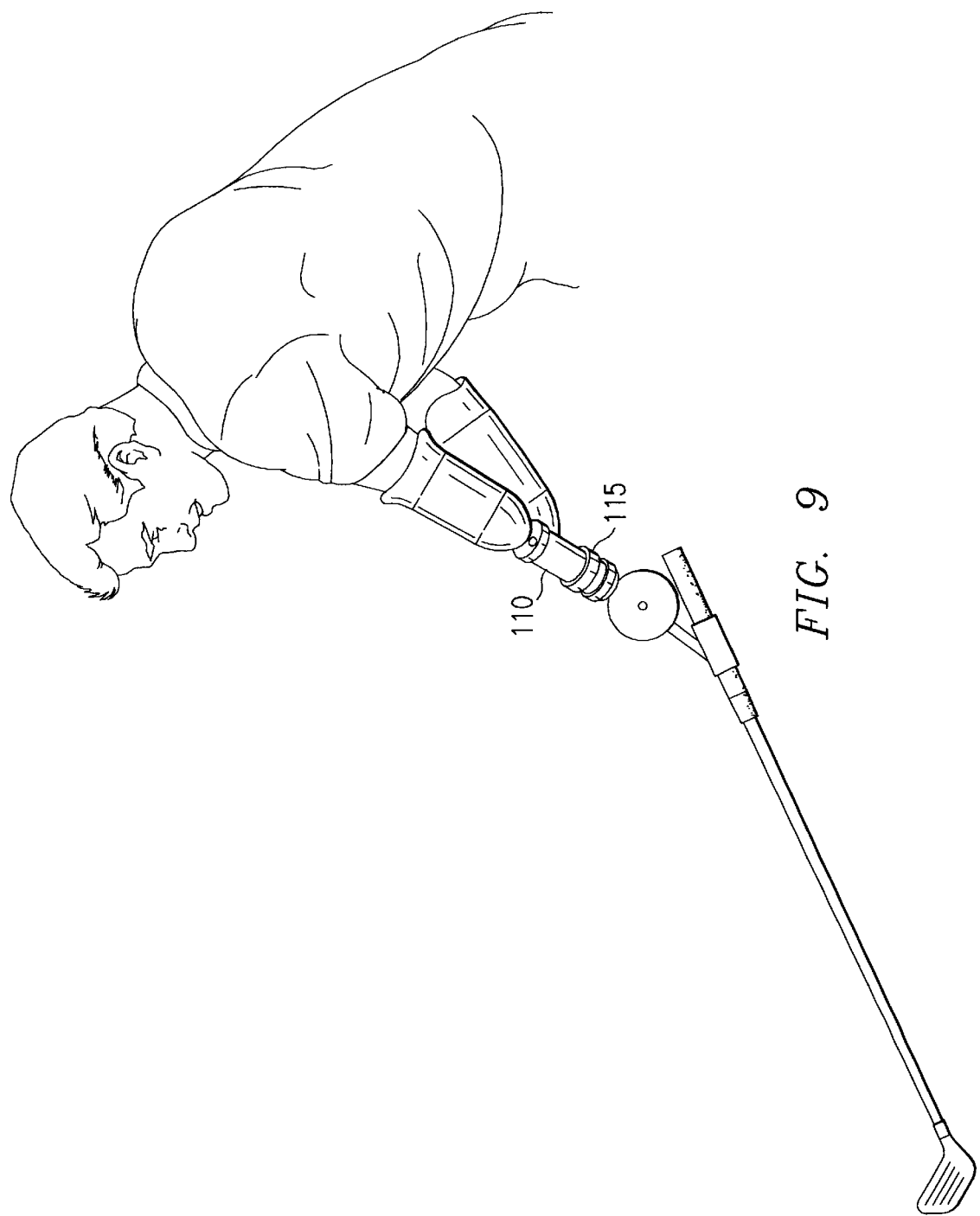

FIG. 9 illustrates take away. It will be seen how the slidable engagement of pylon sleeve 115 on extension pylon 110 assists the amputee in keeping shoulders, back and legs in proper alignment during the amputee's turn for take away.

Figures 10, 10A:
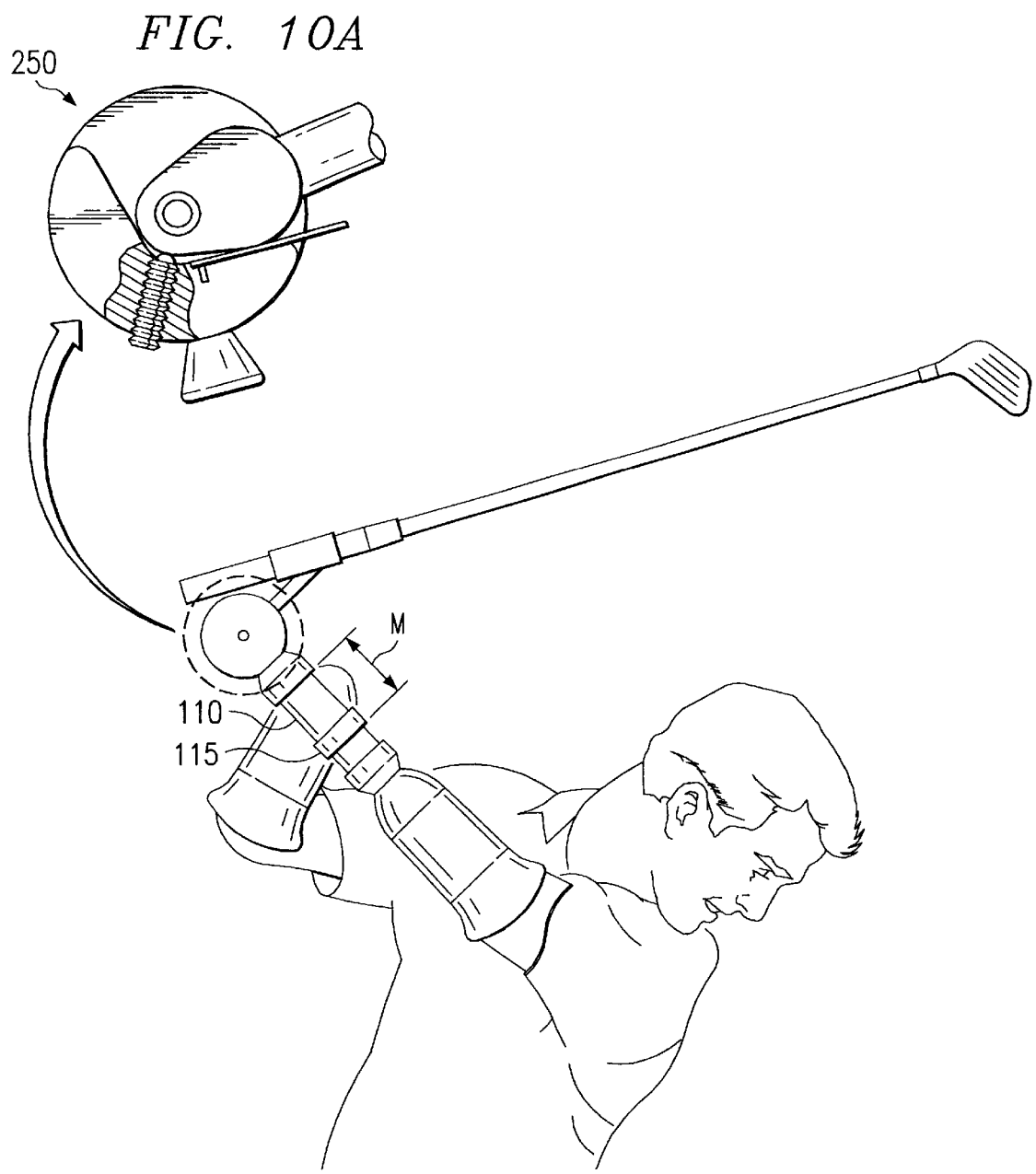

FIG. 10 illustrates the top of the back swing immediately after the amputee has commenced the return swing. As in FIG. 8a, inset FIG. 10a on FIG. 10 illustrates exemplary use of a leaf spring action in rotary joint 250 as described above with respect to FIGS. 6A and 6B. FIG. 10a shows that rotary joint 250 is at maximum deflection of the spring action provided by the leaf spring. It will be understood that the torque exerted on rotary joint 250 by the amputee as the return swing is commenced has caused the deflection, emulating cocking of the wrists in a conventional golf swing. Similarly, as the return swing approaches the ball, the leaf spring in rotary joint 250 as shown in FIG. 10a encourages return to the rest position. This action emulates release of the wrists during the return swing in a conventional golf swing.

It will also be understood from FIGS. 10 and 10a that to execute an optimum swing, the amputee must learn to control the tempo of his or her back swing and return to the ball so that, in combination with the spring action where provided in rotary joint 250, the club advantageously reaches a horizontal attitude at the top of the amputee's back swing. As is well known in the golfing art, a return swing through the ball from this position allows the power of the shoulders, back and legs to combine to generate club head speed immediately before the ball is struck.

It will also be understood from FIGS. 10 and 10a that rotary deflection of the rotary joint 250 against the spring action (where provided) enables the flexure in the golf club's shaft also to be brought into play in generating club head speed, per a conventional golf swing. This is particularly apparent at the top of the amputee's back swing, when the change in direction of swing from back swing to return spring causes the rotating portion 260 of the rotary joint 250 to work hardest against the opposing spring action.

FIG. 10 also illustrates further the effect of the slidable engagement of pylon sleeve 115 on pylon extension 110. The full range of slidable displacement M is illustrated. It will be seen that as the amputee commences a back swing, the shoulders, back and hips start to turn. Emulating the placement of two hands on the golf club, the slidable engagement of the pylon sleeve on the extension pylon along displacement M enables the amputee to keep shoulders, back and hips in proper alignment during back swing and return swing. There is also a more complete transfer of energy into the swing from the shoulders, back and legs. Moreover, although not visible on FIG. 10, it will be understood that the vibration isolator illustrated on FIG. 1 absorbs the impact of the club head hitting the ball, tending to reduce transfer of the impact into the amputee's limb and shoulder.

Although the present invention and its advantages have been described in detail, it should be understood that various changes, substitutions and alterations can be made herein without departing from the spirit and scope of the invention as defined by the appended claims.

We claim:

1. A golf prosthesis for an upper extremity amputee, the prosthesis assisting the amputee to swing a golf club, the prosthesis comprising:
   a prosthetic socket; and
   a wrist terminal device connecting the prosthetic socket to the golf club, the wrist terminal device further including:
      a club holder, the club holder firmly holding the golf club; and
      a rotary joint, the rotary joint permitting selectable predetermined amounts of rotation during back swing and return swing.

2. The golf prosthesis of claim 1, in which the rotary joint is also restrained from rotation in all but a preselected plane, the preselected plane adjustably selectable with respect to the direction in which the amputee desires to hit the ball with the golf club.

3. The golf prosthesis of claim 1, in which the club holder holds the golf club using an attachment method selected from the group consisting of (1) friction, and (2) clamping.

4. The golf prosthesis of claim 1, in which rotation of the rotary joint is encouraged by spring action to return to a rest position in which the golf club extends substantially straight towards a ball and away from the amputee when the amputee addresses the ball before swinging.

5. The golf prosthesis of claim 4, in which the spring action comprises a first spring mechanism encouraging rotation to return to the rest position during back swing.

6. The golf prosthesis of claim 5, in which the rotary joint includes a rotating portion and a stationary portion, and in which the first spring mechanism is operable against the rotating portion via leverage against the stationary portion.

7. The golf prosthesis of claim 5, in which the first spring mechanism includes a spring selected from the group consisting of:
   (a) a leaf spring;
   (b) a ball plunger spring;
   (c) a pneumatic spring;
   (d) a hydraulic spring; and
   (e) a resilient solid material spring
   (f) a cantilever spring.

8. The golf prosthesis of claim 4, in which the spring action further comprises a second spring mechanism encouraging rotation to return to the rest position during return swing.

9. The golf prosthesis of claim 8, in which the rotary joint includes a rotating portion and a stationary portion, and in which the first and second spring mechanisms are operable against the rotating portion via leverage against the stationary portion.

10. The golf prosthesis of claim 8, in which the first and second springs mechanisms each include a spring selected from the group consisting of:
    a leaf spring;
    a ball plunger spring;
    a pneumatic spring;
    a hydraulic spring; and
    a resilent solid material spring
    a cantilever spring.

11. A golf prosthesis of claim 1, further including an adjustable rotation damper mechanism disposed to regulate rotation in response to torque.

12. The golf prosthesis of claim 11, in which the adjustable rotation damper mechanism includes a damper ball plunger spring located in the stationary portion and operable against the rotating portion, the damper ball plunger spring disposed to be adjustably tightenable in frictionally restraining rotation of the rotating portion.

13. A golf prosthesis for an upper extremity amputee, the prosthesis assisting the amputee to swing a golf club, the prosthesis comprising:
    a prosthetic socket; and
    a wrist terminal device connecting the prosthetic socket to the golf club, the wrist terminal device further including:
    a club holder, the club holder firmly holding the golf club;
    a rotary joint, rotation of the rotary joint encouraged by spring action to return to a rest position in which the golf club extends substantially straight towards a ball and away from the amputee when the amputee addresses the ball before swinging; and
    the rotary joint permitting selectable predetermined amounts of rotation against the spring action during back swing and return swing.

14. The golf prosthesis of claim 13, in which the rotary joint is also restrained from rotation in all but a preselected plane, the preselected plane adjustably selectable with respect to the direction in which the amputee desires to hit the ball with the golf club.

15. The golf prosthesis of claim 13, in which the club holder holds the golf club using an attachment method selected from the group consisting of (1) friction, and (2) clamping.

16. The golf prosthesis of claim 13, in which the spring action comprises a first spring mechanism encouraging rotation to return to the rest position during back swing.

17. The golf prosthesis of claim 16, in which the rotary joint includes a rotating portion and a stationary portion, and in which the first spring mechanism is operable against the rotating portion via leverage against the stationary portion.

18. The golf prosthesis of claim 17, in which the first spring mechanism includes a spring selected from the group consisting of:
    (a) a leaf spring;
    (b) a ball plunger spring;
    (c) a pneumatic spring;

(d) a hydraulic spring; and (e) a resilient solid material spring (f) a cantilever spring.

19. The golf prosthesis of claim 17, further including an adjustable rotation damper mechanism disposed to regulate rotation in response to torque.

20. The golf prosthesis of claim 19, in which the adjustable rotation damper mechanism includes a damper ball plunger spring located in the stationary portion and operable against the rotating portion, the damper ball plunger spring disposed to be adjustably tightenable in frictionally restraining rotation of the rotating portion.

21. The golf prosthesis of claim 16, in which the spring action further comprises a second spring mechanism encouraging rotation to return to the rest position during return swing.

22. The golf prosthesis of claim 21, in which the rotary joint includes a rotating portion and a stationary portion, and in which the first and second spring mechanisms are operable against the rotating portion via leverage against the stationary portion.

23. The golf prosthesis of claim 22, in which the first and second springs mechanisms each include a spring selected from the group consisting of:

(a) a leaf spring;

(b) a ball plunger spring;

(c) a pneumatic spring;

(d) a hydraulic spring; and (e) a resilient solid material spring (f) a cantilever spring.

24. The golf prosthesis of claim 21, further including an adjustable rotation damper mechanism disposed to regulate rotation in response to torque.

25. The golf prosthesis of claim 24, in which the adjustable rotation damper mechanism includes a damper ball plunger spring located in the stationary portion and operable against the rotating portion, the damper ball plunger spring disposed to be adjustably tightenable in frictionally restraining rotation of the rotating portion.

26. A golf prosthesis for an upper extremity amputee, the prosthesis assisting the amputee to swing a golf club, the prosthesis comprising:

first and second prosthetic sockets;

an extension pylon extending from the first prosthetic socket towards the golf club, the second prosthetic socket attached to the extension pylon; and a wrist terminal device connecting the extension pylon to the golf club, the wrist terminal device further including:

a club holder, the club holder firmly holding the golf club;

a rotary joint restrained from rotation in all but a preselected plane, the preselected plane adjustably selectable with respect to the direction in which the amputee desires to hit a ball with the golf club; and the rotary joint permitting predetermined amounts of rotation during back swing and return swing.

27. The golf prosthesis of claim 26, in which the club holder holds the golf club using an attachment method selected from the group consisting of (1) friction, and (2) clamping.

28. The golf prosthesis of claim 26, in which rotation of the rotary joint in the preselected plane is encouraged by spring action to return to a rest position in which the golf club extends substantially straight towards the ball and away from the amputee when the amputee addresses the ball before swinging.

29. The golf prosthesis of claim 28, in which the spring action comprises a first spring mechanism encouraging rotation to return to the rest position during back swing.

30. The golf prosthesis of claim 29, in which the rotary joint includes a rotating portion and a stationary portion, and in which the first spring mechanism is operable against the rotating portion via leverage against the stationary portion.

31. The golf prosthesis of claim 28, which the first spring mechanism includes a spring selected from the group consisting of:

(a) a leaf spring;

(b) a ball plunger spring;

(c) a pneumatic spring;

(d) a hydraulic spring; and (e) a resilient solid material spring (f) a cantilever spring.

32. The golf prosthesis of claim 29, in which the spring action further comprises a second spring mechanism encouraging rotation to return to the rest position during return swing.

33. The golf prosthesis of claim 32, in which the rotary joint includes a rotating portion and a stationary portion, and in which the first and second spring mechanisms are operable against the rotating portion via leverage against the stationary portion.

34. The golf prosthesis of claim 33, in which the first and second springs mechanisms each include a spring selected from the group consisting of:

(a) a leaf spring;

(b) a ball plunger spring;

(c) a pneumatic spring;

(d) a hydraulic spring; and (e) a resilient solid material spring (f) a cantilever spring.

35. The golf prosthesis of claim 26, further including an adjustable rotation damper mechanism disposed to regulate rotation in response to torque.

36. The golf prosthesis of claim 35, in which the adjustable rotation damper mechanism includes a damper ball plunger spring located in the stationary portion and operable against the rotating portion, the damper ball plunger spring disposed to be adjustably tightenable in frictionally restraining rotation of the rotating portion.

37. The golf prosthesis of claim 26, in which an upper tube adaptor connects the extension pylon to the first prosthetic socket.

38. The golf prosthesis of claim 37, in which the upper tube adaptor includes screws in a collar disposed to clamp down on faces of a multi-faced lug on the first prosthetic socket.

39. The golf prosthesis of claim 26, in which a lower tube adaptor connects the extension pylon to the wrist terminal device.

40. The golf prosthesis of claim 39, in which the lower tube adaptor includes screws in a collar disposed to clamp down on faces of a multi-faced lug on the wrist terminal device.

41. The golf prosthesis of claim 26, in which said attachment between the second prosthetic socket and the extension pylon is a slidable engagement.

42. The golf prosthesis of claim 41, in which said slidable engagement of the second prosthetic socket upon the extension pylon includes a pylon sleeve disposed to slide along the extension pylon.

43. The golf prosthesis of claim 42, in which the pylon sleeve includes a ring slidably encircling the extension pylon.

44. The golf prosthesis of claim 26, in which said attachment between the second prosthetic socket and the extension pylon includes a vibration isolator.

45. The golf prosthesis of claim 44, in which the vibration isolator includes a resilient vibration damper made from a material selected from the group consisting of:
   (a) an elastomer; and
   (b) rubber.

46. The golf prosthesis of claim 26, in which said attachment between the second prosthetic socket and the extension pylon includes a disconnect mechanism operable by the amputee.

47. The golf prosthesis of claim 46, in which the disconnect mechanism includes a release mechanism selected from the group consisting of:
   (a) a shuttle lock;
   (b) a lever release; and
   (c) a twist release.

48. The golf prosthesis of claim 26, in which said attachment between the second prosthetic socket and the extension pylon is substantially fixed.

49. The golf prosthesis of claim 26, in which said attachment between the second prosthetic socket and the extension pylon further comprises a second extension pylon extending from the second prosthetic socket towards the golf club.

50. A golf prosthesis for an upper extremity amputee, the prosthesis assisting the amputee to swing a golf club, the prosthesis comprising:
   first and second prosthetic sockets;
   an extension pylon extending from the first prosthetic socket towards the golf club, the second prosthetic socket slidably engaged upon the extension pylon, said slidable engagement of the second prosthetic socket upon the extension pylon including a pylon sleeve disposed to slide along the extension pylon and a connector connecting the pylon sleeve to the second prosthetic socket;
   the connector comprising a vibration isolator including a resilient vibration damper made from a material selected from the group consisting of (1) elastomer and (2) rubber; and
   a wrist terminal device connecting the extension pylon to the golf club, the wrist terminal device further including:
      a club holder, the club holder firmly holding the golf club;
      a rotary joint restrained from rotation in all but a preselected plane, the preselected plane adjustably selectable with respect to the direction in which the amputee desires to hit a ball with the golf club;
      rotation in the preselected plane encouraged by spring action to return to a rest position in which the golf club extends substantially straight towards the ball and away from the amputee when the amputee addresses the ball before swinging;
      the spring action comprising first and second spring mechanisms encouraging rotation to return to the rest position during back swing and return swing respectively, each of the first and second spring mechanisms including a spring selected from the group consisting of:
         (a) a leaf spring;
         (b) a ball plunger spring;
         (c) a pneumatic spring;
         (d) a hydraulic spring; and
         (e) a resilient solid material spring;
         (f) a cantilever spring;
      the rotary joint permitting selectable amounts of rotation against the spring action during back swing and return swing, the rotary joint including a rotating portion and a stationary portion, the first and second spring mechanisms each operating upon the rotating portion via leverage against the stationary portion; and
      the rotary joint further including an adjustable rotation damper mechanism disposed to regulate rotation in response to torque, the rotation damper mechanism comprising a damper ball plunger spring located in the stationary portion of the rotary joint and operable against the rotating portion of the rotary joint, the damper ball plunger spring disposed to be adjustably tightenable in frictionally restraining rotation of the rotating portion.

51. The golf prosthesis of claim 50, in which the club holder holds the golf club using an attachment method selected from the group consisting of (1) friction, and (2) clamping.

52. The golf prosthesis of claim 50, in which upper tube adaptor connects the extension pylon to the first prosthetic socket.

53. The golf prosthesis of claim 52, in which the upper tube adaptor includes screws in a collar disposed to clamp down on faces of a multi-faced lug on the first prosthetic socket.

54. The golf prosthesis of claim 50, in which a lower tube adaptor connects the extension pylon to the wrist terminal device.

55. The golf prosthesis of claim 54, in which the lower tube adaptor includes screws in a collar disposed to clamp down on faces of a multi-faced lug on the wrist terminal device.

56. The golf prosthesis of claim 50, in which the pylon sleeve includes a ring slidably encircling the extension pylon.

57. The golf prosthesis of claim 50, in which the connector includes a disconnect mechanism operable by the amputee.

58. The golf prosthesis of claim 57, in which the disconnect mechanism includes a release mechanism selected from the group consisting of:
   (a) a shuttle lock;
   (b) a lever release; and
   (c) a twist release.

59. The golf prosthesis of claim 50, in which the connector further comprises a second extension pylon extending from the second prosthetic socket towards the golf club.

* * * * *